US010499975B2

(12) United States Patent
Ding et al.

(10) Patent No.: US 10,499,975 B2
(45) Date of Patent: Dec. 10, 2019

(54) BIPOLAR SURGICAL INSTRUMENT

(71) Applicant: COVIDIEN LP, Mansfield, MA (US)

(72) Inventors: Weijiang Ding, Shanghai (CN);
Peixiong Yi, Shanghai (CN); Xiucheng Shen, Shanghai (CN); Duane E. Kerr, Loveland, CO (US); Sarfraz Ahamed Syed, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 158 days.

(21) Appl. No.: 14/907,222

(22) PCT Filed: Aug. 7, 2013

(86) PCT No.: PCT/CN2013/080953
§ 371 (c)(1),
(2) Date: Jan. 22, 2016

(87) PCT Pub. No.: WO2015/017994
PCT Pub. Date: Feb. 12, 2015

(65) Prior Publication Data
US 2016/0157924 A1 Jun. 9, 2016

(51) Int. Cl.
*A61B 18/14* (2006.01)
*A61B 18/00* (2006.01)
(Continued)

(52) U.S. Cl.
CPC .. *A61B 18/1442* (2013.01); *A61B 2017/0023* (2013.01); *A61B 2018/0063* (2013.01);
(Continued)

(58) Field of Classification Search
CPC .... A61B 2017/2829; A61B 2017/2948; A61B 18/1442; A61B 2018/146;
(Continued)

(56) References Cited

U.S. PATENT DOCUMENTS

D249,549 S    9/1978  Pike
D263,020 S    2/1982  Rau, III
(Continued)

FOREIGN PATENT DOCUMENTS

CN    201299462      9/2009
CN    102525639 A    7/2012
(Continued)

OTHER PUBLICATIONS

Extended European Search Report corresponding to Int'l Appl. No. EP 13 89 1305.8 dated Feb. 24, 2017.
(Continued)

*Primary Examiner* — Jaymi E Della
*Assistant Examiner* — Sean W Collins
(74) *Attorney, Agent, or Firm* — Carter, DeLuca & Farrell LLP

(57) ABSTRACT

A bipolar forceps includes a mechanical forceps including first and second shafts each having a jaw member extending from a distal end thereof and a handle disposed at a proximal end thereof for effecting movement of the jaw members relative to one another about a pivot. A disposable housing is configured to releasably couple to at least one of the shafts and an electrode assembly is configured to releasably couple to the disposable housing. The electrode assembly includes electrodes releasably coupleable to the jaw members. At least one of the electrodes includes a knife channel configured to receive a knife blade there through to cut tissue grasped between the jaw members. An actuation mechanism is configured to selectively advance the knife blade through the knife channel to cut tissue.

19 Claims, 9 Drawing Sheets

(51) Int. Cl.
*A61B 17/00* (2006.01)
*A61B 18/12* (2006.01)

(52) U.S. Cl.
CPC ............ *A61B 2018/00077* (2013.01); *A61B 2018/00083* (2013.01); *A61B 2018/0094* (2013.01); *A61B 2018/00607* (2013.01); *A61B 2018/00958* (2013.01); *A61B 2018/126* (2013.01); *A61B 2018/142* (2013.01); *A61B 2018/1455* (2013.01); *A61B 2018/1495* (2013.01)

(58) Field of Classification Search
CPC .... A61B 2018/1452; A61B 2018/1455; A61B 2018/0094; A61B 2018/00077; A61B 2017/0023; A61B 2018/126; A61B 2018/00083; A61B 2018/1495; A61B 2018/0063; A61B 2018/00958; A61B 2018/00607
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,499,992 A * | 3/1996 | Meade ............... A61B 17/29 606/170 |
| D384,413 S | 9/1997 | Zlock et al. |
| H1745 H | 4/1998 | Paraschac |
| 5,800,449 A * | 9/1998 | Wales ............... A61B 18/1447 606/170 |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 9,084,608 B2 | 7/2015 | Larson et al. |
| 9,211,657 B2 | 12/2015 | Ackley et al. |
| 9,498,279 B2 | 11/2016 | Artale et al. |
| 2003/0109875 A1* | 6/2003 | Tetzlaff ............... A61B 18/1445 606/48 |
| 2003/0220637 A1 | 11/2003 | Truckai et al. |
| 2004/0236325 A1 | 11/2004 | Tetzlaff et al. |
| 2005/0119655 A1* | 6/2005 | Moses ............... A61B 18/1442 606/51 |
| 2005/0159745 A1 | 7/2005 | Truckai et al. |
| 2010/0179545 A1* | 7/2010 | Twomey ............ A61B 18/1445 606/51 |
| 2012/0083786 A1 | 4/2012 | Artale et al. |
| 2012/0172873 A1* | 7/2012 | Artale ............... A61B 18/1442 606/46 |
| 2013/0041370 A1 | 2/2013 | Unger |
| 2013/0046295 A1 | 2/2013 | Kerr et al. |
| 2013/0138101 A1 | 5/2013 | Kerr |
| 2014/0221994 A1 | 8/2014 | Reschke |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2016/0157925 A1 | 6/2016 | Artale et al. |

FOREIGN PATENT DOCUMENTS

| | | |
|---|---|---|
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |

(56) References Cited

FOREIGN PATENT DOCUMENTS

| | | |
|---|---|---|
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 | 6/2002 |
| WO | 02080786 A1 | 10/2002 |
| WO | 02080793 A1 | 10/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |
| WO | 2013/009758 A2 | 1/2013 |
| WO | 2013/022928 A1 | 2/2013 |

OTHER PUBLICATIONS

Chinese First Office Action corresponding to counterpart Int'l Appln. No. CN 201410384505.2 dated Apr. 19, 2017.

"Automatically Controlled Bipolar Electrocoagulation—COA-COMP", Neurosurg. Rev. (1984), pp. 187-190.

Michael Choti, "Abdominoperineal Resection with the LigaSure Vessel Sealing System and LigaSure Atlas 20 cm Open Instrument" ; Innovations That Work, Jun. 2003. (4 pages).

Chung et al., "Clinical Experience of Sutureless Closed Hemorrhoidectomy with LigaSure" Diseases of the Colon & Rectum vol. 46, No. 1 Jan. 2003, pp. 87-92.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).

Peterson et al. "Comparison of Healing Process Following Ligation with Sutures and Bipolar Vessel Sealing" Surgical Technology International (2001). (8 pages).

"Electrosurgery: A Historical Overview" Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004. (1 page).

E. David Crawford "Evaluation of a New Vessel Sealing Device in Urologic Cancer Surgery" Sales/Product Literature 2000. (1 page).

Johnson et al. "Evaluation of the LigaSure Vessel Sealing System in Hemorrhoidectormy" American College of Surgeons (ACS) Clinicla Congress Poster (2000). (1 page).

Muller et al., "Extended Left Hemicolectomy Using the LigaSure Vessel Sealing System" Innovations That Work, Sep. 1999. (4 pages).

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002. (4 pages).

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002. (4 pages).

Koyle et al., "Laparoscopic Palomo Varicocele Ligation in Children and Adolescents" Pediatric Endosurgery & Innovative Techniques, vol. 6, No. 1, 2002, pp. 15-19.

W. Scott Helton, "LigaSure Vessel Sealing System: Revolutionary Hemostasis Product for General Surgery"; Sales/Product Literature 1999. (1 page).

LigaSure Vessel Sealing System, the Seal of Confidence in General, Gynecologic, Urologic, and Laparoscopic Surgery; Sales/Product Literature; Apr. 2002. (8 pages).

(56) References Cited

OTHER PUBLICATIONS

Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Seyfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004. (1 page).
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000. (1 page).
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000. (4 pages).
Levy et al. "Use of a New Energy-based Vessel Ligation Device During Vaginal Hysterectomy" Int'l Federation of Gynecology and Obstetrics (FIGO) World Congress 1999. (1 page).
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000. (1 page).
Jarrett et al., "Use of the LigaSure Vessel Sealing System for Peri-Hilar Vessels in Laparoscopic Nephrectomy" Sales/Product Literature 2000. (1 page).
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.. (1 page).
McLellan et al. "Vessel Sealing for Hemostasis During Gynecologic Surgery" Sales/Product Literature 1999. (1 page).
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremcich.
Heniford et al. "Initial Research and Clinical Results with an Electrothermal Bipolar Vessel Sealer" Oct. 1999. (1 page).
European Examination Report issued in Appl. No. EP 13 891 305.8 dated Feb. 21, 2018 (6 pages).
Australian Examination Report dated Sep. 20, 2017 in Appl. No. AU 2015264858 (4 pages).
Chinese Second Office Action issued in Appln. No. CN 201410384505.2 dated Dec. 6, 2017, together with English translation (14 pages).
Notification of Third Office Action issued by the Chinese Patent Office in Appl. No. CN 201410384505.2 dated May 15, 2018, together with English language translation (9 pages).
Canadian Office Action issued in corresponding Appl. No. CA 2,918,484 dated Feb. 28, 2019 (4 pages).

\* cited by examiner

BIPOLAR SURGICAL INSTRUMENT

CROSS REFERENCE TO RELATED APPLICATION

The present application is a U.S. National Stage Application under 35 U.S.C. § 371(a) of PCT/CN2013/080953 filed Aug. 7, 2013, the entire contents of which are incorporated by reference herein.

BACKGROUND

1. Background of Related Art

The present disclosure relates to forceps used for open surgical procedures. More particularly, the present disclosure relates to a bipolar forceps for treating tissue that is capable of sealing and cutting tissue.

2. Technical Field

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Certain surgical procedures require sealing and cutting blood vessels or vascular tissue. Several journal articles have disclosed methods for sealing small blood vessels using electrosurgery. An article entitled Studies on Coagulation and the Development of an Automatic Computerized Bipolar Coagulator, J. Neurosurg., Volume 75, Jul. 1991, describes a bipolar coagulator which is used to seal small blood vessels. The article states that it is not possible to safely coagulate arteries with a diameter larger than 2 to 2.5 mm. A second article is entitled Automatically Controlled Bipolar Electrocoagulation—"COA-COMP", Neurosurg. Rev. (1984), pp. 187-190, describes a method for terminating electrosurgical power to the vessel so that charring of the vessel walls can be avoided.

By utilizing an electrosurgical forceps, a surgeon can either cauterize, coagulate/desiccate, reduce or slow bleeding and/or seal vessels by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

SUMMARY

The present disclosure relates to forceps used for open surgical procedures. More particularly, the present disclosure relates to a bipolar forceps for treating tissue that is capable of sealing and cutting tissue.

As is traditional, the term "distal" refers herein to an end of the apparatus that is farther from an operator, and the term "proximal" refers herein to the end of the electrosurgical forceps that is closer to the operator.

The bipolar forceps includes a mechanical forceps including first and second shafts. A jaw member extends from a distal end of each shaft. A handle is disposed at a proximal end of each shaft for effecting movement of the jaw members relative to one another about a pivot from a first position wherein the jaw members are disposed in spaced relation relative to one another to a second position wherein the jaw members cooperate to grasp tissue. A disposable housing is configured to releasably couple to one or both of the shafts. An electrode assembly is associated with the disposable housing and has a first electrode releasably coupleable to the jaw member of the first shaft and a second electrode releasably coupleable to the jaw member of the second shaft. Each electrode is adapted to connect to a source of electrosurgical energy to allow selective conduction of electrosurgical energy through tissue. One or both of the electrodes includes a knife channel defined along its length. The knife channel is configured to receive a knife blade therethrough to cut tissue grasped between the jaw members. An actuation mechanism is at least partially disposed within the housing and configured to selectively advance the knife blade through the knife channel to cut tissue.

Additionally or alternatively, the bipolar forceps may also include a knife lockout mechanism configured to prohibit advancement of the knife blade into the knife channel when the jaw members are in the first position.

Additionally or alternatively, the knife lockout mechanism may move from a first position wherein the knife lockout mechanism engages the actuation mechanism when the jaw members are in the first position to a second position wherein the knife lockout mechanism disengages the actuation mechanism when the jaw members are in the second position to permit selective advancement of the knife blade through the knife channel.

Additionally or alternatively, at least one of the shafts may be configured to engage the knife lockout mechanism upon movement of the jaw members to the second position and move the knife lockout mechanism out of engagement with the actuation mechanism to permit advancement of the knife blade through the knife channel.

Additionally or alternatively, the bipolar forceps may also include at least one depressible button supported by the housing configured to selectively deliver electrosurgical energy to the electrodes.

Additionally or alternatively, the pivot may define a longitudinal slot therethrough and the knife blade may be configured to move within the longitudinal slot upon translation thereof.

Additionally or alternatively, the bipolar forceps may also include at least one handle member extending from the housing. The at least one handle member may be operably coupled to the actuation mechanism and configured to effect advancement of the knife blade through the knife channel.

Additionally or alternatively, each of the electrodes may include an electrically conductive sealing surface and an insulating substrate coupled thereto.

Additionally or alternatively, each of the electrodes may include at least one mechanical interface configured to complement a corresponding mechanical interface on one of the jaw members to releasably couple the electrode to the jaw member.

Additionally or alternatively, the actuation mechanism may include a biasing member configured to bias the actuation mechanism to an unactuated position.

Additionally or alternatively, the bipolar forceps may also include a knife guide supported in the housing and having a longitudinal slot defined therethrough that receives the knife blade therein to align the knife blade with the knife channel.

According to another aspect of the present disclosure, a bipolar forceps is provided. The bipolar forceps includes a mechanical forceps including first and second shafts each having a jaw member extending from its distal end. A handle is disposed at a proximal end of each shaft for effecting movement of the jaw members relative to one another about a pivot from a first position wherein the jaw members are disposed in spaced relation relative to one another to a second position wherein the jaw members cooperate to grasp tissue. A disposable housing has opposing halves configured to releasably couple to each other to at least partially encompass one or both of the shafts. An electrode assembly is associated with the disposable housing and has a first electrode releasably coupleable to the jaw member of the first shaft and a second electrode releasably coupleable to the jaw member of the second shaft. Each electrode is adapted to connect to a source of electrosurgical energy to allow selective conduction of electrosurgical energy through tissue held therebetween. At least one of the electrodes includes a knife channel defined along a length thereof, the knife channel configured to receive a knife blade therethrough to cut tissue grasped between the jaw members. An actuation mechanism is at least partially disposed within the housing and is configured to selectively advance the knife blade through the knife channel to cut tissue. A knife lockout mechanism is configured to move from a first position wherein the knife lockout mechanism engages the actuation mechanism to prohibit advancement of the knife blade through the knife channel when the jaw members are in the first position to a second position wherein the knife lockout mechanism disengages the actuation mechanism when the jaw members are in the second position to permit advancement of the knife blade through the knife channel.

Additionally or alternatively, at least one of the shafts may be configured to engage the knife lockout mechanism upon movement of the jaw members to the second position and move the knife lockout mechanism out of engagement with the actuation mechanism and permit advancement of the knife blade through the knife channel.

Additionally or alternatively, the pivot may define a longitudinal slot therethrough and the knife blade may be configured to advance through the longitudinal slot upon translation thereof.

Additionally or alternatively, the bipolar forceps may also include a knife guide supported in the housing and having a longitudinal slot defined therethrough that receives the knife blade therein to align the knife blade with the knife channel.

Additionally or alternatively, the bipolar forceps may also include at least one handle member configured to effect advancement of the knife blade through the knife channel. The at least one handle member may extend from the housing and may be operably coupled to the actuation mechanism.

According to another aspect of the present disclosure, a bipolar forceps is provided. The bipolar forceps includes a mechanical forceps including first and second shafts each having a jaw member extending from its distal end. A handle is disposed at a proximal end of each shaft for effecting movement of the jaw members relative to one another about a pivot from a first position wherein the jaw members are disposed in spaced relation relative to one another to a second position wherein the jaw members cooperate to grasp tissue therebetween. A disposable housing is configured to be releasably coupled to at least one of the shafts. An electrode assembly is configured to releasably couple to the jaw members and is adapted to connect to a source of electrosurgical energy to allow selective conduction of electrosurgical energy through tissue held between the jaw members. At least one of the jaw members includes a knife channel defined along its length. The knife channel is configured to receive a knife blade therethrough to cut tissue grasped between the jaw members. A knife guide is supported in the housing and has a longitudinal slot defined therethrough that receives the knife blade therein to align the knife blade with the knife channel. An actuation mechanism is at least partially disposed within the housing and is configured to selectively advance the knife blade through the knife channel to cut tissue. At least one handle member extends from the housing. The at least one handle member is operably coupled to the actuation mechanism and is configured to effect advancement of the knife blade through the knife channel. A knife lockout mechanism is configured to be engaged by at least one of the shaft members and move the knife lockout mechanism from a first position wherein the knife lockout mechanism engages the actuation mechanism to prohibit advancement of the knife blade into the knife channel when the jaw members are in the first position to a second position wherein the knife lockout mechanism disengages the actuation mechanism when the jaw members are in the second position to permit selective advancement of the knife blade through the knife channel.

Additionally or alternatively, the knife guide may extend through a longitudinal slot defined through the pivot.

Additionally or alternatively, the at least one handle member may be moveable from a first position wherein the knife blade is disposed within the housing to a second position wherein the knife blade is advanced through the knife channel.

Additionally or alternatively, the actuating mechanism may include a biasing member configured to bias the at least one movable handle from the second position to the first position.

BRIEF DESCRIPTION OF THE DRAWINGS

Various embodiments of the subject instrument are described herein with reference to the drawings wherein.

DETAILED DESCRIPTION

Figure 1:
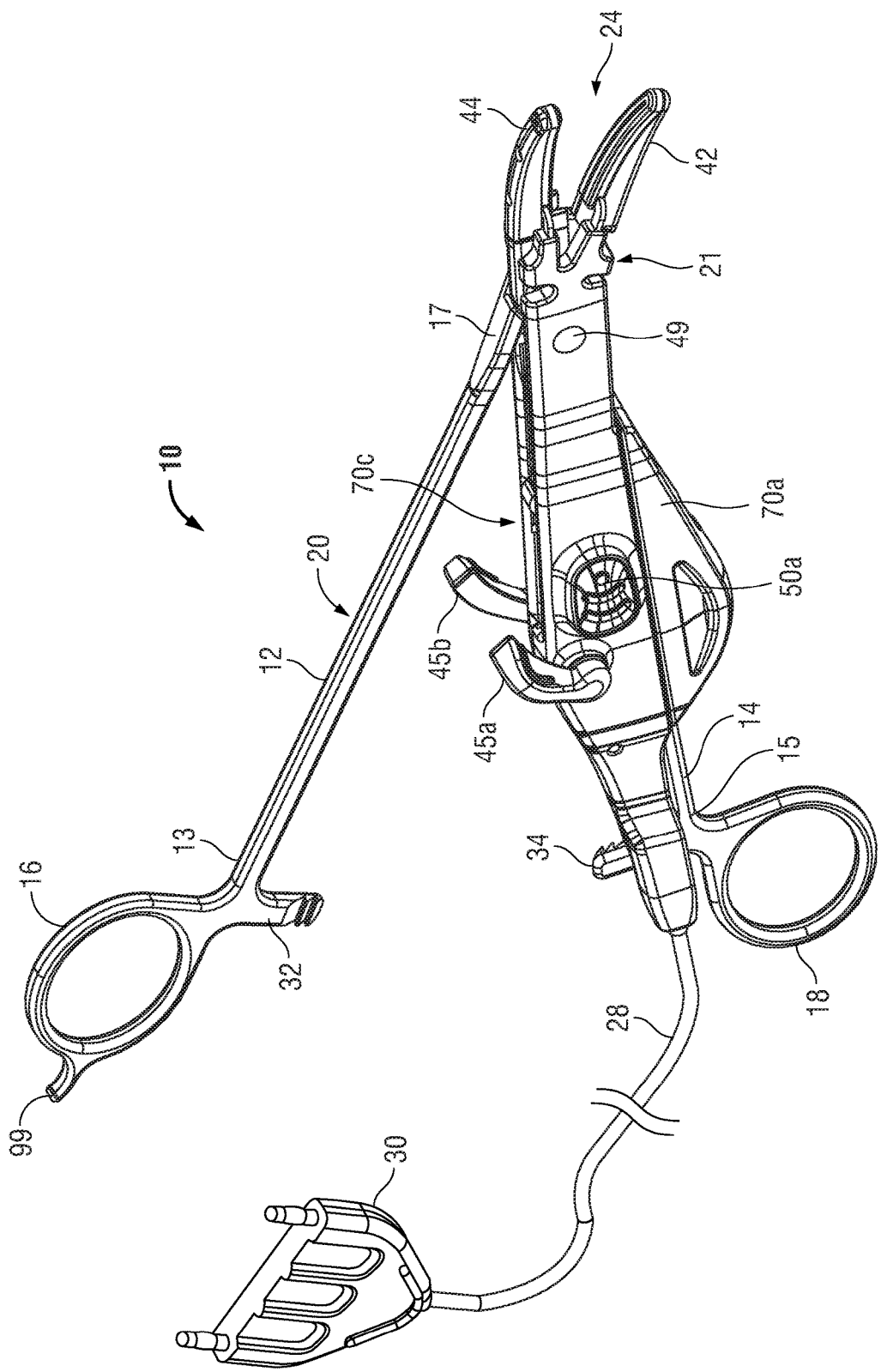
FIG. 1 is a perspective view of a bipolar forceps according to an embodiment of the present disclosure including a mechanical forceps, a disposable housing, and a disposable electrode assembly.
Figure 2:
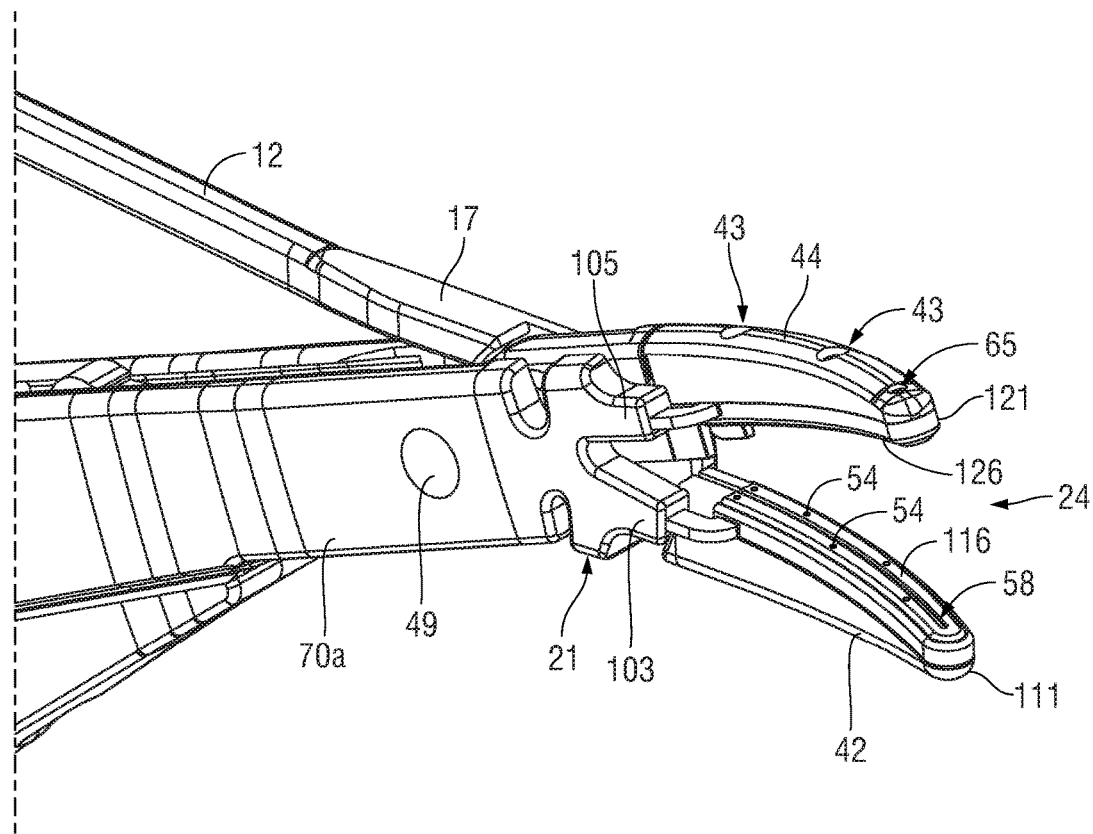
FIG. 2 is an enlarged, perspective view of a distal end of the bipolar forceps of FIG. 1.
Figure 3:
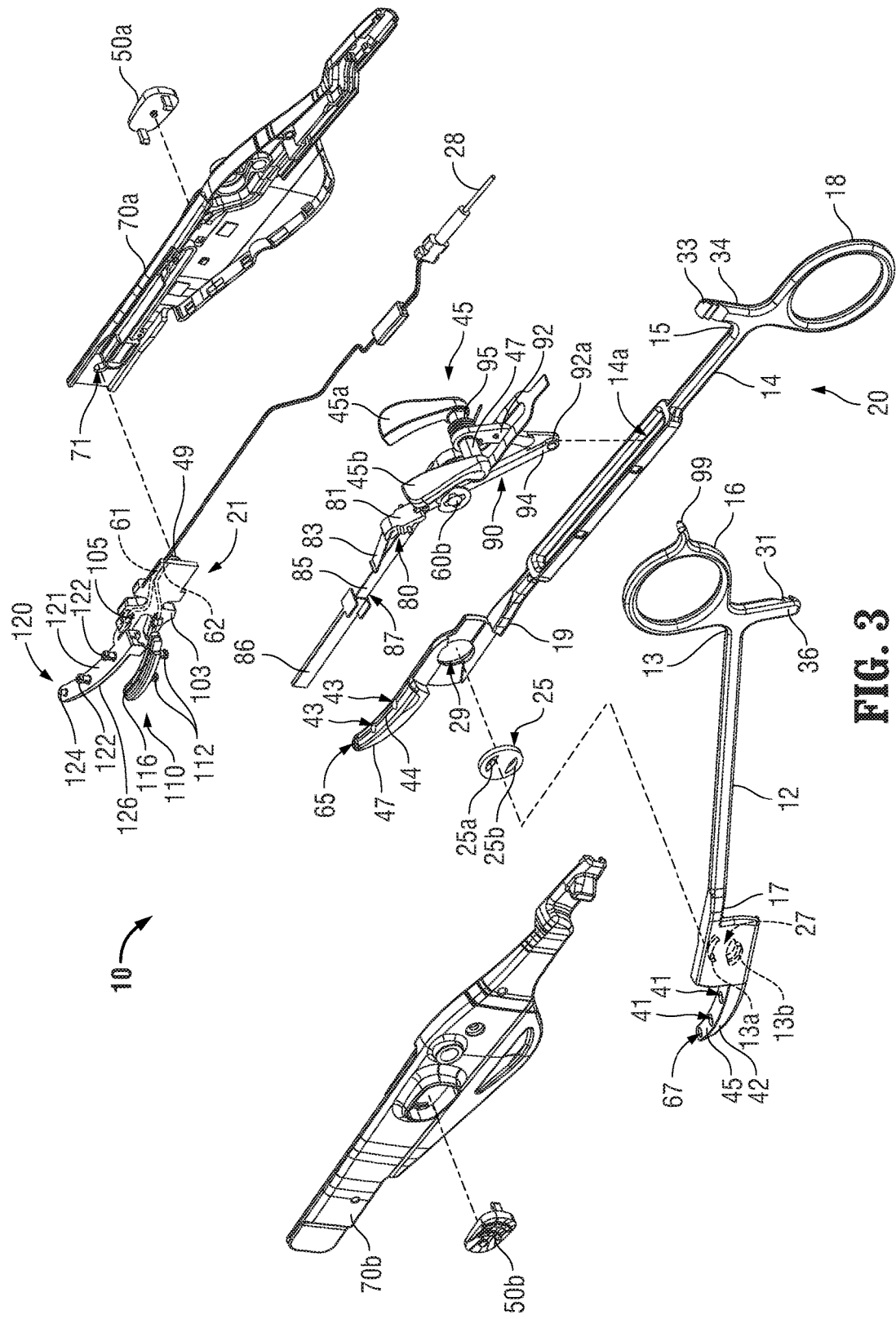
FIG. 3 is a perspective view of the bipolar forceps of FIG. 1 with parts separated.

Referring initially to FIGS. 1-3, a bipolar forceps 10 for use with open surgical procedures includes a mechanical forceps 20 having an end effector 24 and a disposable electrode assembly 21. Mechanical forceps 20 includes first and second elongated shaft members 12 and 14. Elongated shaft member 12 includes proximal and distal end portions 13 and 17, respectively, and elongated shaft member 14 includes proximal and distal end portions 15 and 19, respectively. Disposed at proximal end portions 13, 15 of shaft members 12, 14 are handle members 16 and 18, respectively, that are configured to allow a user to effect movement of at least one of the shaft members 12 and 14 relative to the other. The end effector 24 includes opposing jaw members 42, 44 that extend from the distal end portions 17 and 19 of shaft members 12 and 14, respectively. The jaw members 42, 44 are movable relative to each other in response to movement of shaft members 12, 14.

Shaft members 12 and 14 are affixed to one another about a pivot 25 such that movement of shaft members 12, 14, imparts movement of the jaw members 42, 44 from a first configuration (FIG. 9A) wherein the jaw members 44, 42 are disposed in spaced relation relative to one another, e.g., an open configuration, to a second configuration (FIGS. 9B and 9C) wherein the jaw members 42, 44 cooperate to grasp tissue 150 therebetween (FIG. 8), e.g., a clamping or closed configuration. In some embodiments, the forceps 10 may be configured such that movement of one or both of the shaft members 12, 14 causes only one of the jaw members to move with respect to the other jaw member. Pivot 25 includes a pair of generally semi-circular shaped apertures 25a, 25b disposed therethrough and is configured to be seated in a pivot aperture 29 (FIG. 3) such that pivot 25 is permitted to freely rotate within pivot aperture 29, as further detailed below.

Each shaft member 12 and 14 also includes a ratchet portion 32 and 34, respectively. Each ratchet 32, 34 extends from the proximal end portion 13, 15 of its respective shaft member 12, 14 towards the other ratchet in a generally vertically aligned manner such that the inner facing surfaces of each ratchet 32 and 34 abut one another when the shaft members 12, 14 are approximated. Each ratchet 32 and 34 includes a plurality of flanges 31 and 33 (FIG. 3), respectively, that project from the inner facing surface of each ratchet 32 and 34 such that the ratchets 32 and 34 may interlock at one or more positions. In some embodiments, each ratchet position holds a particular strain energy in the shaft members 12 and 14 to impart a specific closure force to the end effector 24. At least one of the shaft members, e.g., shaft member 12, includes a tang 99 that facilitates manipulation of forceps 20 during surgical conditions as well as facilitates attachment of electrode assembly 21 on mechanical forceps 20 as will be described in greater detail below.

Referring to FIGS. 2 and 3, disposable electrode assembly 21 is configured to releasably couple to mechanical forceps 20, as detailed below, and is operably coupled to a housing 70 having a pair of housing halves 70a, 70b configured to matingly engage and releasably encompass at least a portion of shaft member 14. Housing 70 also serves to house a knife 85 having a sharpened distal cutting edge 89 (FIG. 9C), a knife guide 86 having a longitudinal slot 87 (FIG. 3) configured to receive the knife blade 85 therein, and a knife actuation mechanism 90 (FIG. 3) configured to effect advancement of the knife blade 85 through a knife channel 58 (FIG. 2) defined in one or both electrodes 110, 120 to transect tissue, as further detailed below. An interior of each of housing half 70a, 70b may include a plurality of cooperating mechanical interfaces disposed at various positions to effect mechanical coupling of housing halves 70a, 70b to form housing 70.

Figure 4:
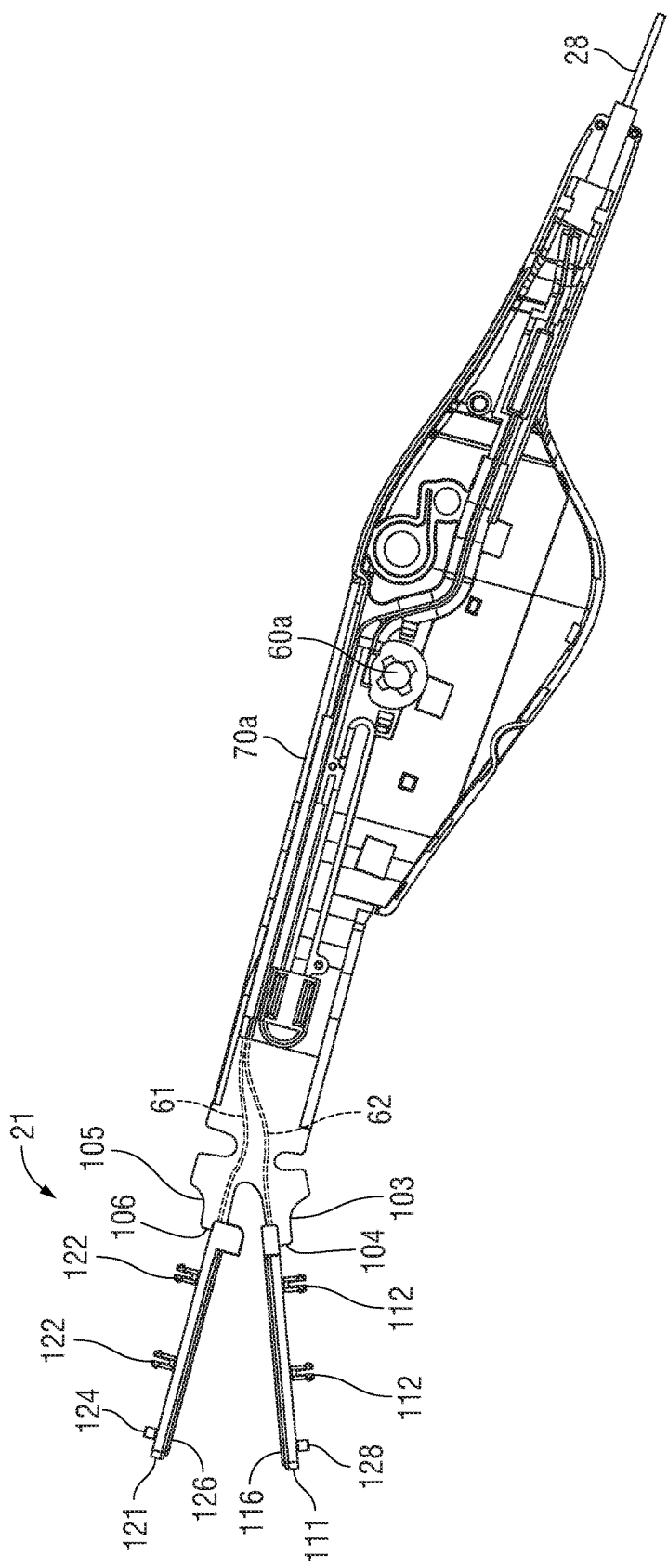
FIG. 4 is an enlarged, internal side view of the disposable housing and the disposable electrode assembly of FIG. 1 with parts partially removed.
Figure 6:
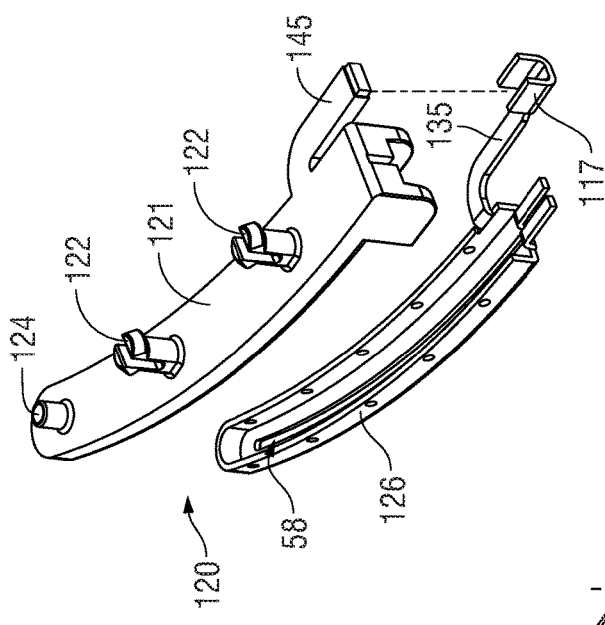
FIGS. 6 and 7 are greatly-enlarged perspective views of electrodes of the disposable electrode assembly of FIG. 1 with parts separated.
Figure 5:
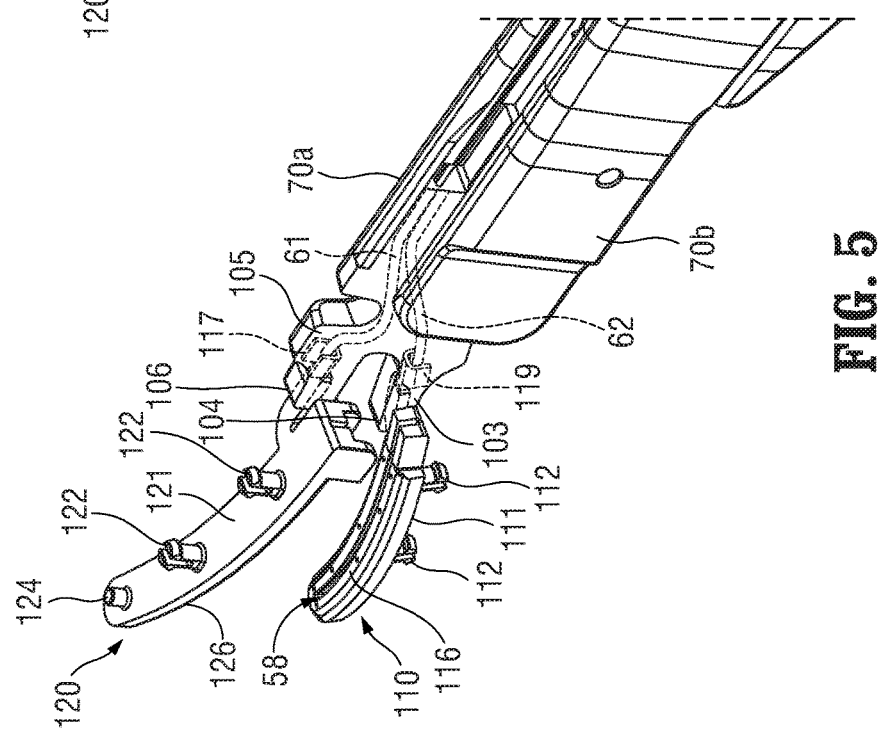
FIG. 5 is a greatly-enlarged, perspective view of the disposable electrode assembly of FIG. 1.

As shown in FIGS. 4 and 5, a pair of wires 61 and 62 are electrically connected to the electrodes 120 and 110, respectively, and are bundled to form a cable 28 that extends through housing 70 and terminates at a terminal connector 30 (FIGS. 1 and 3) configured to mechanically and electrically couple to a suitable energy source such as an electrosurgical generator (not shown). One example of an electrosurgical generator is the LIGASURE® Vessel Sealing Generator and the ForceTriad® Generator sold by Covidien. In some embodiments, one or both of handle members 16 and 18 may include a suitable mechanical interface (e.g., a wire holder) configured to releasably retain cable 28 to aid in keeping cable 28 from interfering with a surgeon's hands during operation of forceps 10.

Referring now to FIGS. 3-7, electrode assembly 21 includes a generally circular boss member 49 configured to be seated (e.g., friction fit) within a complementary aperture 71 disposed through a distal end of housing half 70a to releasably attach electrode assembly 21 thereto. Electrode assembly 21 is bifurcated such that two prong-like members 103 and 105 extend distally therefrom to support electrodes 110 and 120, respectively. Electrode 120 includes an electrically conductive sealing surface 126 configured to conduct electrosurgical energy therethrough and an electrically insulative substrate 121 that serves to electrically insulate jaw member 42 from sealing surface 126. Sealing surface 126 and substrate 121 are attached to one another by any suitable method of assembly such as, for example, snap-fit engagement or by overmolding substrate 121 to sealing surface 126. In some embodiments, substrate 121 is made from an injection molded plastic material. Substrate 121 includes a plurality of bifurcated anchor members 122 extending therefrom that are configured to compress during insertion into a corresponding plurality of sockets 43 disposed at least partially through an inner facing surface 47 (FIG. 3) of jaw member 44 and subsequently expand to releasably engage corresponding sockets 43 after insertion to couple electrode 120 to inner facing surface 47. Substrate 121 also includes an alignment pin 124 (FIG. 6) that is configured to engage an aperture 65 disposed at least partially through inner facing surface 47 of jaw member 44 to ensure proper alignment of electrode 120 with jaw member 44 during assembly. Conductive sealing surface 126 includes an extension 135 having a wire crimp 117 configured to be inserted into the distal end 106 of prong 105 of electrode assembly 21 and electrically connect to wire 61 disposed therein (FIG. 5).

Figure 7:
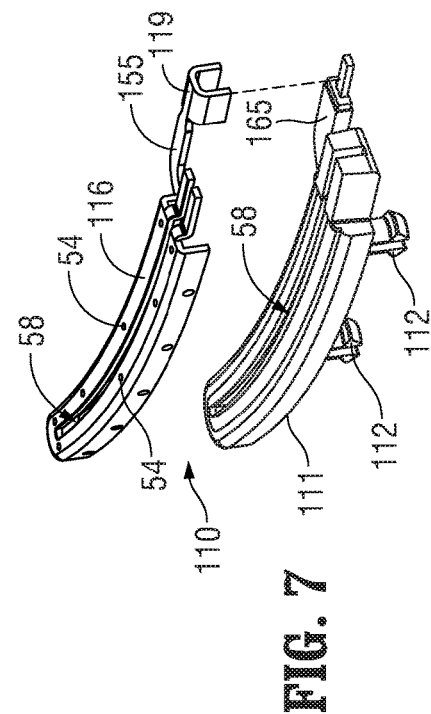

Substantially as described above with respect to electrode 120, electrode 110 includes an electrically conductive sealing surface 116 configured to conduct electrosurgical energy therethrough and an electrically insulative substrate 111 attached thereto, as shown in FIG. 7. Substrate 111 includes a plurality of bifurcated anchor members 112 extending therefrom that are configured to compress during insertion into a corresponding plurality of sockets 41 disposed at least partially through an inner facing surface 45 (FIG. 3) of jaw member 42 and subsequently expand to releasably engage corresponding sockets 41 after insertion to couple electrode 110 to inner facing surface 45. Substrate 111 also includes an alignment pin 128 (FIG. 4) that is configured to engage an aperture 67 disposed at least partially through inner facing surface 45 of jaw member 42 to ensure proper alignment of electrode 110 with jaw member 42 during assembly. Sealing surface 116 includes an extension 155 having a wire crimp 119 extending therefrom configured to be inserted into the distal end 104 of prong 103 of electrode assembly 21 and electrically connect to wire 62 disposed therein. Substrate 111 includes an extension 165 extending proximally therefrom and configured to couple to extension 155 of sealing surface 116.

Referring to FIG. 4, at least one of the prong members 103, 105 is flexible such that prong members 105 and 103 are readily moveable relative to each other. In some embodiments, the electrode assembly 21 is removably attached to the mechanical forceps 20 by initially moving prongs 103, 105 towards each other. While jaw members 42, 44 are in an open configuration, the electrodes 120 and 110 may be slid between opposing jaw members 44 and 42 such that anchor members 122 and 112 and guide pins 124 and 128, respectively, may be aligned with and releasably inserted into corresponding sockets 43 and 41 or apertures 65 and 67, respectively, to couple electrodes 120 and 110 with jaw members 44 and 42, respectively. Housing halves 70a, 70b may then be releasably coupled to form housing 70 to encompass at least a portion of shaft member 14 in the manner described above.

To electrically control the end effector 24, the housing 70 supports a pair of depressible activation buttons 50a, 50b that are operable by the user to actuate corresponding switches 60a, 60b, respectively, disposed within housing 70. Although not explicitly shown, switches 60a, 60b are electrically interconnected with wires 61, 62, respectively, and serve to initiate and terminate the delivery of electrosurgical energy from a suitable energy source to the end effector 24 to effect a tissue seal.

Once a tissue seal is established, the knife blade 85 may be advanced through the knife channel 58 to transect the sealed tissue, as detailed below. However, in some embodiments, knife blade 85 may be advanced through the knife channel 58 before, during, or after tissue sealing. In some embodiments, a knife lockout mechanism 80 is provided to prevent extension of the knife blade 85 into the knife channel 58 when the jaw members 42, 44 are in the open configuration, thus preventing accidental or premature transection of tissue, as detailed below.

Figure 9A:
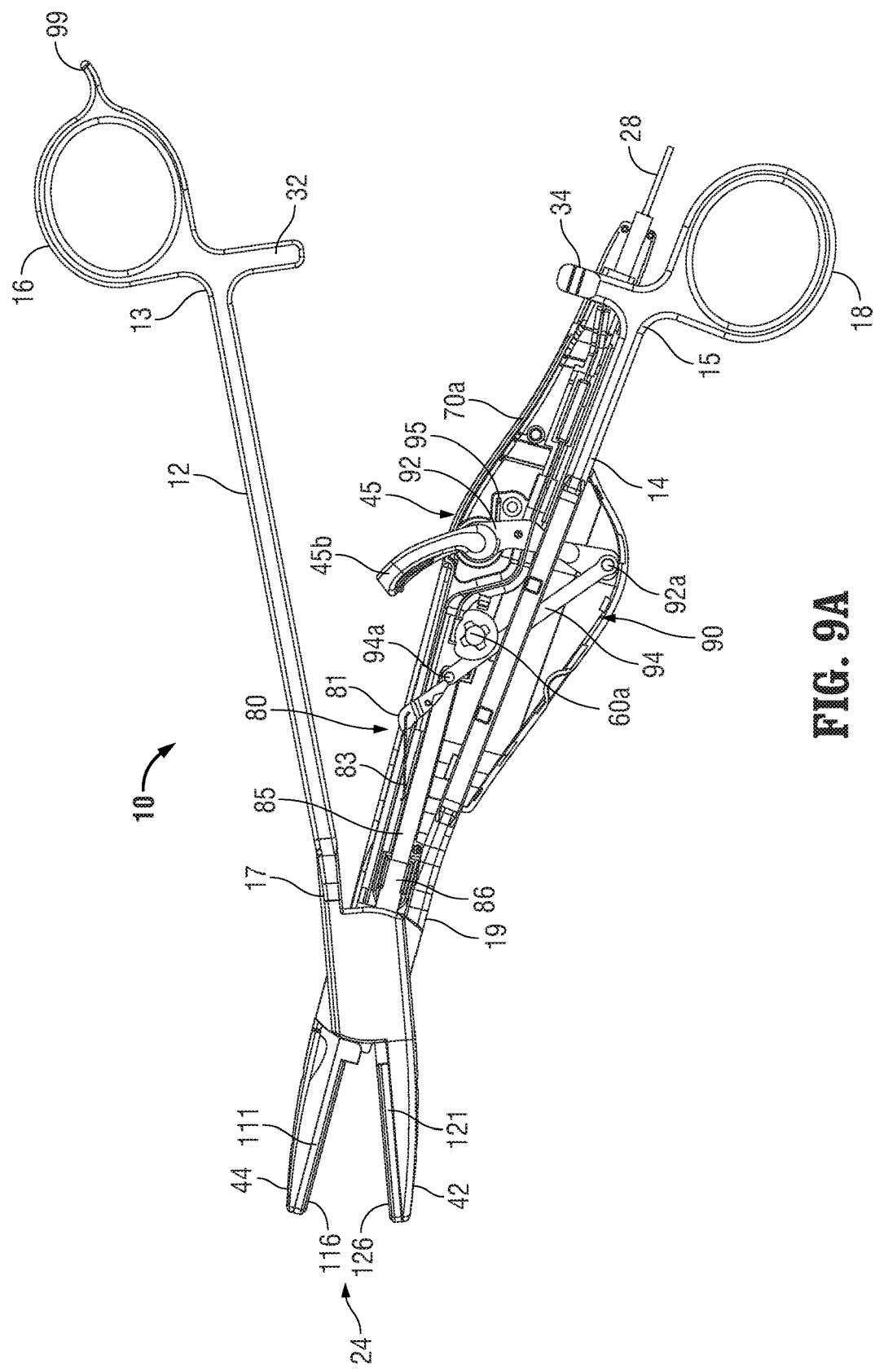
FIGS. 9A-9C are generally internal, side views of the bipolar forceps of FIG. 1 depicting a sequence of motions to illustrate operation of the bipolar forceps.

With reference to FIG. 3, the knife actuation mechanism 90 is operably associated with a trigger 45 having opposing handle members 45a, 45b extending from opposing sides of housing 70. Upon actuation of handle members 45a, 45b, the knife actuation mechanism 90 responds utilizing a series of inter-cooperating elements to actuate the knife blade 85 through the knife channel 58 to sever tissue grasped between jaw members 42, 44, as detailed below with reference to FIG. 9C. More specifically, the knife actuation mechanism 90 includes a first link 92 operably coupled at one end to a shaft member 47 and at an opposing end to a second link 94 by a pivot pin 92a. Shaft member 47 extends laterally through housing 70 to operably connect handle members 45a, 45b from opposing sides of housing 70. The second link 94 is operably coupled at one end to the first link 92 by the pivot pin 92a and at the other end to a proximal end of the knife blade 85 by a pivot pin 94a (FIG. 9A). Shaft member 14 defines a longitudinal slot 14a therethrough that is configured to receive first and second links 92, 94 therein. First and second links 92, 94 extend through longitudinal slot 14a and are free to move therethrough upon actuation of the handle members 45a, 45b, as further detailed below with reference to FIG. 9C.

Figure 9B:
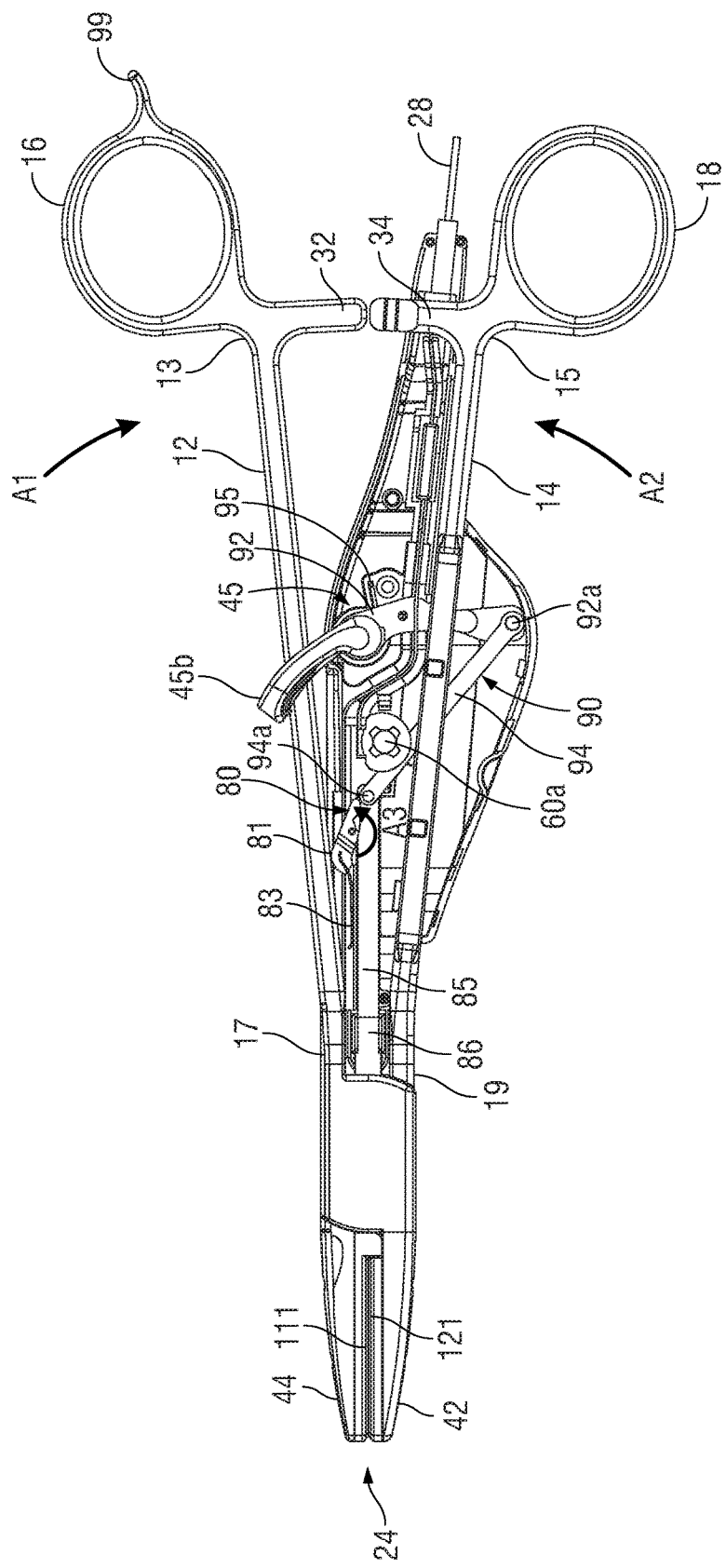

A biasing member 95 (e.g., torsion spring) is disposed coaxially about at least a portion of the shaft member 47 between the first link 92 and handle member 45a. The biasing member 95 is operably coupled at one end to a portion of the first link 92 and at the other end to a suitable mechanical interface within the housing 70 that braces or stabilizes biasing member 95 during use of the knife actuation mechanism 90. The biasing member 95 serves to bias the trigger 45 such that subsequent to actuation of the knife blade 85 through the knife channel 58 (FIG. 9C), handle members 45a, 45 are biased to return to an unactuated position (FIGS. 9A and 9B), thereby retracting the knife blade 85 proximally to an unactuated position (FIGS. 9A and 9B).

With reference to FIG. 3, pivot 25 includes a pair of apertures 25a, 25b disposed therethrough that are configured to receive a pair of complementary raised portions 13a, 13b therein, respectively, extending from the distal end portion 17 of shaft member 12 and defining a longitudinal passageway 27 therebetween. Raised portions 13a, 13b extend sufficiently from the distal portion of shaft member 14 so that apertures 25a, 25b may receive raised portions 13a, 13b therein, respectively, while maintaining pivot 25 in spaced relation with the distal portion of shaft member 14 to allow the knife guide 86 to be received through passageway 27. Movement of shaft members 12, 14 relative to each other causes rotational movement of pivot 25 within pivot aperture 29.

A knife guide 86 is supported within the housing 70 between the end effector 24 and the knife actuation mechanism 90 and extends through passageway 27. The longitudinal slot 87 of the knife guide 86 provides lateral support to the knife blade 85 and constrains side-to-side lateral motion of the knife blade 85. Thus, the distal knife guide 86 serves to urge the knife blade 85 into a central position relative to end effector 24, thereby ensuring proper alignment of the knife blade 85 as the knife blade 85 enters the knife channel 58 (FIG. 2) defined in electrodes 110, 120.

Figure 9C:
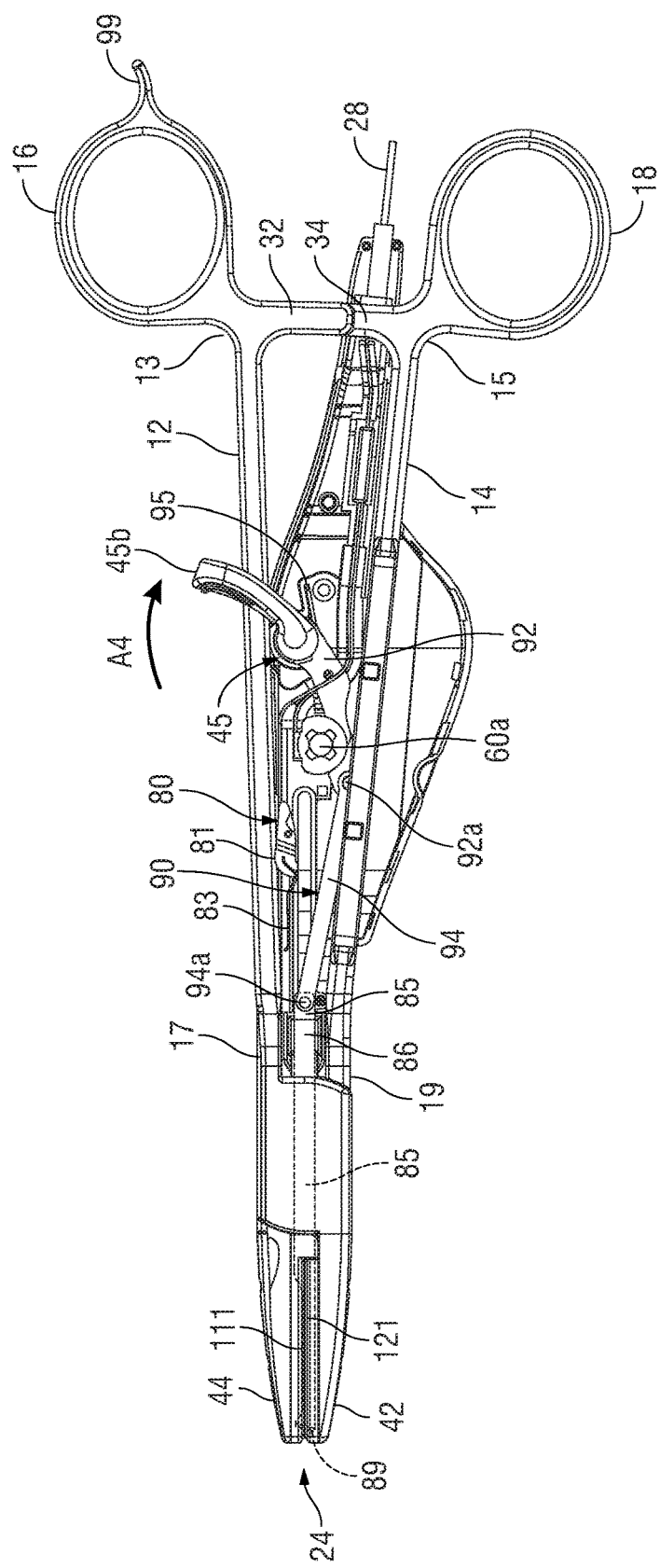

In some embodiments, the forceps 10 includes a knife blade lockout mechanism 80 supported within the housing 70 and that serves to prevent advancement of the knife blade 85 into the knife channel 85 when the jaw members 42, 44 are in the open configuration (FIG. 9A). With reference to FIG. 3, the knife blade lockout mechanism 80 includes a safety link 81 operably coupled with a biasing member 83 (e.g., a leaf spring) and pivotally supported within the housing 70. In the open configuration of jaw members 42, 44, the knife blade 85 is in an unactuated position (FIGS. 9A and 9B) and the safety link 81 is engaged with pivot pin 94a (FIG. 9A) such that distal advancement of knife blade 85 is prohibited. As shown in FIG. 1, housing 70 includes a longitudinal opening 70c that opposes shaft member 12 and exposes the knife blade lockout mechanism 80 such that upon approximation of the shaft members 12, 14 to move the jaw members 42, 44 to the closed position (FIG. 9B), safety link 81 is engaged by shaft member 12. Pressure applied to safety link 81 by approximation of shaft members 12, 14 operates to bias the biasing member 83 against the knife blade 85 and, in turn, rotate the safety link 81 out of engagement with the pivot pin 94a (FIG. 9B) such that knife blade 85 is permitted to advance distally into the knife channel 58 (FIG. 9C). Operation of the knife actuation mechanism 90, the knife lockout mechanism 80, and actuation of the knife blade 85 is further detailed below with reference to FIGS. 9A-9C.

The tissue seal thickness and tissue seal effectiveness may be influenced by the pressure applied to tissue between jaw members 44, 42 and the gap distance between the opposing electrodes 110 and 120 (FIG. 5) during tissue sealing. In the closed configuration, a separation or gap distance "G" may be maintained between the sealing surfaces 116, 126 by an array of stop members 54 (FIG. 2) disposed on one or both of sealing surfaces 116, 126 (only shown disposed on sealing surface 126 for purposes of illustration). The stop members 54 contact the sealing surface on the opposing jaw member and prohibit further approximation of the sealing surfaces 116, 126. In some embodiments, to provide an effective tissue seal, an appropriate gap distance of about 0.001 inches to about 0.010 inches and, desirably, between about 0.002 and about 0.005 inches may be provided. In some embodiments, the stop members 54 are constructed of an electrically non-conductive plastic or other material molded onto the sealing surfaces 116, 126, e.g., by a process such as overmolding or injection molding. In other embodiments, the stop members 54 are constructed of a heat-resistant ceramic deposited onto sealing surfaces 116, 126.

Figure 8:
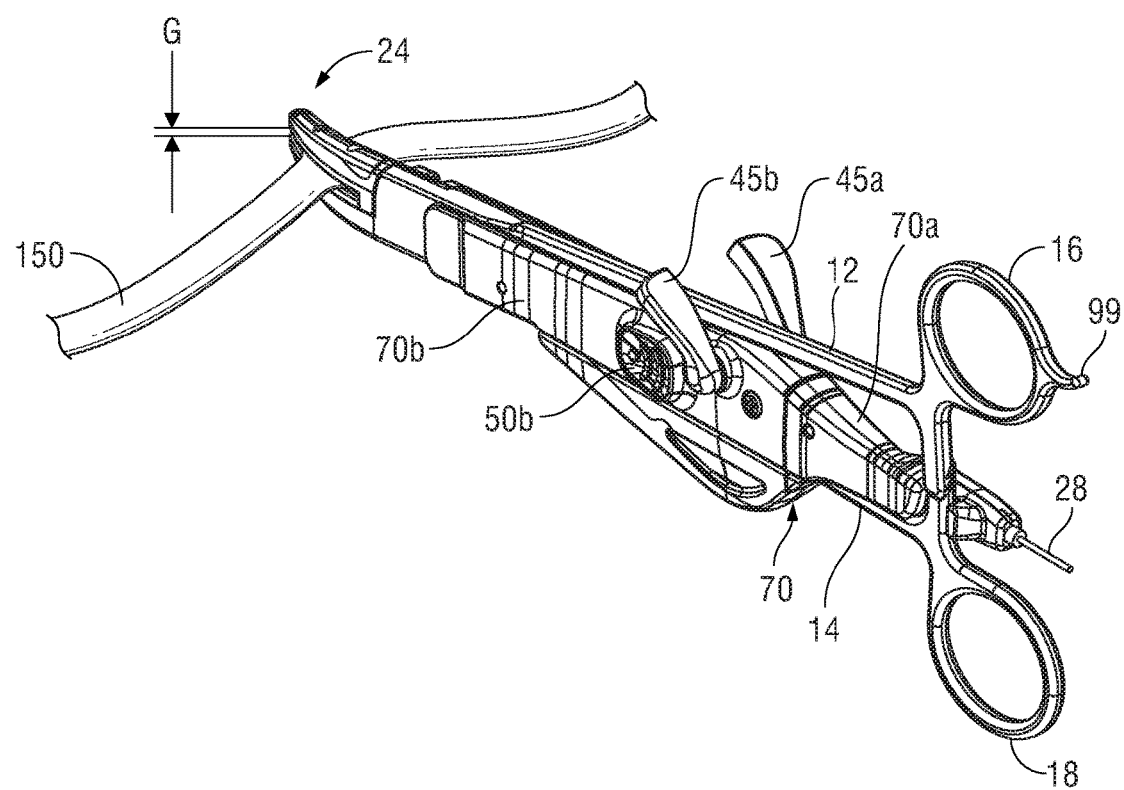
FIG. 8 is a perspective view of the bipolar forceps of FIG. 1 grasping tissue to effect a tissue seal.

FIG. 8 shows the bipolar forceps 10 during use wherein the shaft members 12 and 14 are approximated to apply clamping force to tissue 150 and to effect a tissue seal. Once sealed, tissue 150 may be cut along the tissue seal through actuation of the knife blade 85, as detailed below with reference to FIGS. 9A-9C.

In some embodiments, the performance of forceps 10 may be tested using a virtual tissue vessel. More specifically, the user may place a virtual tissue vessel between sealing surfaces 116, 126 and apply a clamping force to the vessel. The virtual tissue vessel may be, for example, any suitable plastic having impedance. The user may seal the virtual tissue vessel using electrosurgical energy from a suitable electrosurgical generator, e.g., LIGASURE® Vessel Sealing Generator and the ForceTriad® Generator sold by Covidien. The user may also actuate the handle members 45a, 45b to advance the knife blade 85 through the knife channel 58 to cut the sealed virtual tissue vessel. In this scenario, the electrosurgical generator may be configured to automatically run a test procedure that serves to sense the applied clamping force, the gap distance between the opposing electrodes 110, 120, and/or the impedance of the virtual tissue vessel before, during, or after sealing. From this sensed information, the electrosurgical generator may serve to verify that the forceps 10 is in proper working condition (e.g., proper clamping force, gap distance, etc.) following assembly of the electrode assembly 21 to the mechanical forceps 20 and prior to use of the assembled forceps 10 in a vessel sealing procedure.

Referring now to FIGS. 9A, 9B, and 9C, a sequence of motions may be initiated by moving the shaft members 12, 14 in order to close the jaw members 42, 44, and by rotating the handle members 45a, 45b to induce the knife actuation mechanism 90 to translate the knife blade 85 through the knife channel 58. Initially, shaft members 12, 14 are in the open configuration and the handle members 45a, 45b are in an un-actuated position as depicted in FIG. 9A. This arrangement of shaft members 12, 14 and handle members 45a, 45b sustains the end effector 24 in the open configuration wherein the jaw members 42, 44 are substantially spaced from one another, and the knife blade 85 is in a retracted or proximal position with respect to the jaw members 42, 44. The initial position of the handle members 45a, 45b depicted in FIGS. 9A and 9B is actively maintained by the influence of the biasing member 95 on the trigger 45. When jaw members 42, 44 are in the open configuration, as depicted in FIG. 9A, safety link 81 is engaged with pivot pin 94a such that rotational motion of the handle members 45a, 45b in a proximal direction (depicted by rotational arrow A4 in FIG. 9C) is prohibited so that knife blade 85 is prohibited from advancing into knife channel 58.

The jaw members 42, 44 may be moved from the open configuration of FIG. 9A to the closed configuration depicted in FIG. 9B. As the shaft members 12, 14 pivot about pivot 25 in the directions of arrows A1 and A2 (FIG. 9B), respectively, shaft member 12 engages safety link 81. As the shaft members 12, 14 pivot further about pivot 25 in the directions of arrows A1 and A2, respectively, shaft member 12 applies a force on the safety link 81 that causes biasing member 83 to flex against the bias of knife blade 85, thereby inducing rotation of the safety link 81 in the direction depicted by rotational arrow A3 in FIG. 9B. Rotation of safety link 81 in the direction of rotational arrow A3 operates to move the safety link 81 out of engagement with pivot pin 94a as shown in FIG. 9C.

Upon movement of the safety link 81 out of engagement with the pivot pin 94a, handle members 45a, 45b may be selectively moved from the unactuated configuration of FIGS. 9A and 9B to the actuated position of FIG. 9C to advance the knife blade 85 distally through knife channel 58. More specifically, as handle members 45a, 45b rotate in the general proximal direction, depicted by rotational arrow A4, to the actuated configuration depicted in FIG. 9C, the first link 92 imparts a rotational force on second link 94, thereby causing second link 94 to rotate about pivot pin 94a and move in a general distal direction to advance knife blade 85 distally into the knife channel 58.

In some embodiments, the knife actuation mechanism 90 may be positioned relative to shaft member 14 different than the depiction of knife actuation mechanism 90 in FIG. 3. For example, if the knife actuation mechanism 90 depicted in FIG. 3 is disposed substantially between shaft members 14 and 12, then in some embodiments, knife actuation mechanism 90 may be disposed on an opposing side of shaft member 14 such that shaft member 14 is disposed between knife actuation mechanism 90 and shaft member 12. In this scenario, shaft members 12, 14 may be alternatively configured to allow knife blade 85 to advance through longitudinal passageway 27 defined by raised portions 13a, 13b (e.g., via knife guide 86) and into knife channel 58. For example, the distal ends 17, 19 of shaft members 12, 14, respectively, may be configured in various interlocking relationships (e.g., a lock-box configuration) that facilitate the knife 85 entering the knife channel 58 in various orientations relative to shaft members 12, 14 and/or knife channel 58.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A bipolar forceps, comprising:
a mechanical forceps including first and second shafts each having a jaw member extending from a distal end thereof and a handle disposed at a proximal end thereof for effecting movement of the jaw members relative to one another about a pivot from a first position wherein the jaw members are disposed in spaced relation relative to one another to a second position wherein the jaw members cooperate to grasp tissue therebetween, wherein a portion of the first shaft is bifurcated to define a longitudinal slot;
a disposable housing releasably coupled to the first shaft such that the longitudinal slot defined by the bifurcated portion of the first shaft is disposed within the disposable housing;
an electrode assembly associated with the disposable housing and having a first electrode releasably coupleable to the jaw member of the first shaft and a second electrode releasably coupleable to the jaw member of the second shaft, the first electrode and the second electrode adapted to connect to a source of electrosurgical energy to allow selective conduction of the electrosurgical energy through the tissue held therebetween;
at least one of the first or second electrodes including a knife channel defined along a length thereof, the knife channel configured to receive a knife blade therethrough to cut the tissue grasped between the jaw members;
a longitudinal passageway defined between the first and second shafts;
a knife guide at least partially disposed within a portion of a longitudinal passageway defined by the pivot, the knife guide configured to receive the knife blade therethrough; and
an actuation mechanism at least partially disposed within the disposable housing and configured to move through the longitudinal slot defined by the bifurcated portion of the first shaft to selectively advance the knife blade through the knife channel to cut the tissue.

2. The bipolar forceps according to claim 1, further comprising a knife lockout mechanism configured to prohibit advancement of the knife blade into the knife channel when the jaw members are in the first position.

3. The bipolar forceps according to claim 2, wherein the knife lockout mechanism moves from a first position wherein the knife lockout mechanism engages the actuation mechanism when the jaw members are in the first position to a second position wherein the knife lockout mechanism disengages the actuation mechanism when the jaw members are in the second position to permit selective advancement of the knife blade through the knife channel.

4. The bipolar forceps according to claim 2, wherein at least one of the first or second shafts is configured to engage the knife lockout mechanism upon movement of the jaw members to the second position and move the knife lockout mechanism out of engagement with the actuation mechanism to permit advancement of the knife blade through the knife channel.

5. The bipolar forceps according to claim 1, further comprising at least one depressible button supported by the disposable housing configured to selectively deliver the electrosurgical energy to the first and second electrodes.

6. The bipolar forceps according to claim 1, wherein the knife blade is configured to move within the longitudinal passageway defined between the first and second shafts.

7. The bipolar forceps according to claim 1, further comprising at least one handle member configured to effect advancement of the knife blade through the knife channel, the at least one handle member extending from the disposable housing and operably coupled to the actuation mechanism.

8. The bipolar forceps according to claim 1, wherein each of the first and second electrodes includes an electrically conductive sealing surface and an insulating substrate coupled thereto.

9. The bipolar forceps according to claim 1, wherein each of the first and second electrodes includes at least one mechanical interface configured to complement a corresponding mechanical interface on one of the jaw members to releasably couple the first and second electrodes to the jaw members.

10. The bipolar forceps according to claim 1, wherein the actuation mechanism includes a biasing member configured to bias the actuation mechanism to an unactuated position.

11. The bipolar forceps according to claim 1, wherein the knife guide is supported in the disposable housing and includes a longitudinal slot defined therethrough that receives the knife blade therein to align the knife blade with the knife channel.

12. The bipolar forceps according to claim 1, wherein the actuating mechanism includes a rotatable link disposed within the disposable housing and a rotatable trigger extending from the disposable housing, the rotatable link having a distal end portion pivotably coupled to the knife blade and a proximal end portion pivotably coupled to the rotatable trigger, the rotatable link configured to move through the longitudinal slot defined by the bifurcated portion of the first shaft upon rotation of the rotatable trigger.

13. A bipolar forceps, comprising:
a mechanical forceps including first and second shafts each having a jaw member extending from a distal end thereof and a handle disposed at a proximal end thereof for effecting movement of the jaw members relative to one another about a pivot from a first position wherein the jaw members are disposed in spaced relation relative to one another to a second position wherein the jaw members cooperate to grasp tissue therebetween, wherein a portion of the first shaft is bifurcated to define a longitudinal slot;
a disposable housing having opposing halves releasably coupled to each other to at least partially encompass the first shaft such that the longitudinal slot defined by the bifurcated portion of the first shaft is disposed within the disposable housing;
an electrode assembly associated with the disposable housing and having a first electrode releasably coupleable to the jaw member of the first shaft and a second electrode releasably coupleable to the jaw member of the second shaft, the first electrode and the second electrode adapted to connect to a source of electrosurgical energy to allow selective conduction of the electrosurgical energy through the tissue held therebetween;
at least one of the first or second electrodes including a knife channel defined along a length thereof, the knife channel configured to receive a knife blade therethrough to cut the tissue grasped between the jaw members;
a longitudinal passageway defined between the first and second shafts;

a knife guide at least partially disposed within a portion of a longitudinal passageway defined by the pivot, the knife guide configured to receive the knife blade therethrough;

an actuation mechanism at least partially disposed within the disposable housing and configured to move through the longitudinal slot defined by the bifurcated portion of the first shaft to selectively advance the knife blade through the knife channel to cut the tissue; and a knife lockout mechanism configured to move from a first position wherein the knife lockout mechanism engages the actuation mechanism to prohibit advancement of the knife blade through the knife channel when the jaw members are in the first position to a second position wherein the knife lockout mechanism disengages the actuation mechanism when the jaw members are in the second position to permit advancement of the knife blade through the knife channel.

14. The bipolar forceps according to claim 13, wherein at least one of the first or second shafts is configured to engage the knife lockout mechanism upon movement of the jaw members to the second position and move the knife lockout mechanism out of engagement with the actuation mechanism to permit advancement of the knife blade through the knife channel.

15. The bipolar forceps according to claim 13, wherein the knife blade is configured to advance through the longitudinal passageway defined between the first and second shafts.

16. The bipolar forceps according to claim 13, wherein the knife guide is supported in the disposable housing and includes a longitudinal slot defined therethrough that receives the knife blade therein to align the knife blade with the knife channel.

17. The bipolar forceps according to claim 13, further comprising at least one handle member configured to effect advancement of the knife blade through the knife channel, the at least one handle member extending from the disposable housing and operably coupled to the actuation mechanism.

18. A bipolar forceps, comprising:

a mechanical forceps including first and second shafts each having a jaw member extending from a distal end thereof and a handle disposed at a proximal end thereof for effecting movement of the jaw members relative to one another about a pivot from a first position wherein the jaw members are disposed in spaced relation relative to one another to a second position wherein the jaw members cooperate to grasp tissue therebetween, wherein a portion of the first shaft is bifurcated to define a longitudinal slot;

a disposable housing releasably coupled to the first shaft such that the longitudinal slot defined by the bifurcated portion of the first shaft is disposed within the disposable housing;

an electrode assembly configured to releasably couple to the jaw members and adapted to connect to a source of electrosurgical energy to allow selective conduction of the electrosurgical energy through the tissue held between the jaw members;

at least one of the jaw members including a knife channel defined along a length thereof, the knife channel configured to receive a knife blade therethrough to cut the tissue grasped between the jaw members;

a longitudinal passageway defined between the first and second shafts;

a knife guide supported in the disposable housing and at least partially disposed within a portion of a longitudinal passageway defined by the pivot, the knife guide having a longitudinal slot defined therethrough that receives the knife blade therein to align the knife blade with the knife channel;

an actuation mechanism at least partially disposed within the disposable housing and configured to move through the longitudinal slot defined by the bifurcated portion of the first shaft to selectively advance the knife blade through the knife channel to cut the tissue;

at least one handle member extending from the disposable housing, the at least one handle member operably coupled to the actuation mechanism and configured to effect advancement of the knife blade through the knife channel; and a knife lockout mechanism configured to be engaged by at least one of the first or second shafts and move the knife lockout mechanism from a first position wherein the knife lockout mechanism engages the actuation mechanism to prohibit advancement of the knife blade into the knife channel when the jaw members are in the first position to a second position wherein the knife lockout mechanism disengages the actuation mechanism when the jaw members are in the second position to permit selective advancement of the knife blade through the knife channel.

19. The bipolar forceps according to claim 18, wherein the at least one handle member is moveable from a first position wherein the knife blade is disposed within the disposable housing to a second position wherein the knife blade is advanced through the knife channel.

* * * * *

UNITED STATES PATENT AND TRADEMARK OFFICE
CERTIFICATE OF CORRECTION

PATENT NO. : 10,499,975 B2
APPLICATION NO. : 14/907222
DATED : December 10, 2019
INVENTOR(S) : Ding et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 209 days.

Signed and Sealed this
Thirteenth Day of December, 2022

*Katherine Kelly Vidal*

Katherine Kelly Vidal
*Director of the United States Patent and Trademark Office*